United States Patent [19]

Saito et al.

[11] Patent Number: 4,985,529

[45] Date of Patent: * Jan. 15, 1991

[54] THERMOSETTABLE IMIDE COMPOUND AND EPOXY RESIN COMPOSITION CONTAINING THE SAME

[75] Inventors: Yasuhisa Saito, Higashiosaka; Shuichi Kanagawa, Osaka; Katsuya Watanabe, Takatsuki; Kumimasa Kamio, Suita, all of Japan

[73] Assignee: Sumitomo Chemical Company, Ltd., Osaka, Japan

[*] Notice: The portion of the term of this patent subsequent to Dec. 27, 2005 has been disclaimed.

[21] Appl. No.: 343,252

[22] Filed: Apr. 26, 1989

Related U.S. Application Data

[60] Division of Ser. No. 146,684, Jan. 21, 1988, Pat. No. 4,871,832, which is a continuation-in-part of Ser. No. 890,652, Jul. 30, 1986, abandoned.

[30] Foreign Application Priority Data

Jul. 31, 1985 [JP] Japan ................... 60-170052
Mar. 12, 1986 [JP] Japan ................... 61-53922

[51] Int. Cl.$^5$ .................................. C08G 59/44
[52] U.S. Cl. ................................ 528/96; 525/423; 528/117; 528/322
[58] Field of Search ............... 528/96, 117, 322; 525/423

[56] References Cited

U.S. PATENT DOCUMENTS

| | | | |
|---|---|---|---|
| 3,501,443 | 3/1970 | DiLeone | 260/78 |
| 3,574,160 | 4/1971 | Hsu | 260/30.4 |
| 3,607,814 | 9/1971 | DiLeone | 260/30.4 N |
| 3,634,325 | 1/1972 | DiLeone | 260/47 CP |
| 3,763,114 | 10/1973 | Saluti et al. | 260/78.4 R |
| 4,271,079 | 6/1981 | Maeda et al. | 260/346.3 |
| 4,374,214 | 2/1983 | Holub et al. | 528/117 X |
| 4,487,894 | 12/1984 | Lee | 525/423 |
| 4,794,148 | 12/1988 | Nakamura et al. | 525/423 X |

FOREIGN PATENT DOCUMENTS 1137086 12/1968 United Kingdom .

Primary Examiner—Earl Nielsen
Attorney, Agent, or Firm—Wenderoth, Lind & Ponack

[57] ABSTRACT

The invention provides an imide compound represented by the general formula (I),

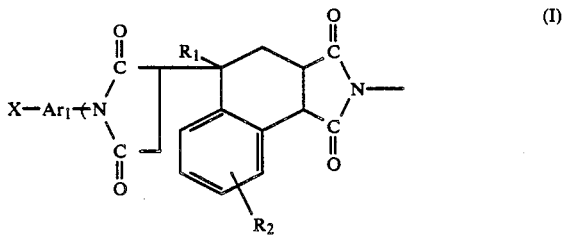

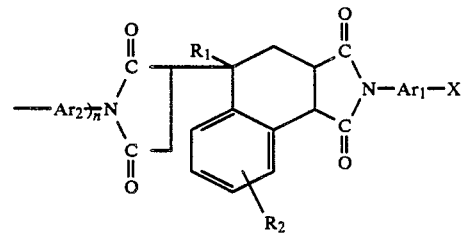

wherein X represents a hydroxyl or amino group, $Ar_1$ and $Ar_2$ independently represent an aromatic residue, $R_1$ represents a hydrogen atom or a $C_1$–$C_{10}$ alkyl group, $R_2$ represents a hydrogen atom, a $C_1$–$C_{20}$ alkyl or alkoxy group or a hydroxyl group, and n represents a number of from 0 to 6, and also provides an epoxy resin composition containing the imide compound (B) and epoxy resins (A) as essential components.

6 Claims, No Drawings

THERMOSETTABLE IMIDE COMPOUND AND EPOXY RESIN COMPOSITION CONTAINING THE SAME

This application is a division of application Ser. No. 146,684, filed Jan. 21, 1988 (now U.S. Pat. No. 4,871,832), which application is a continuation-in-part of Ser. No. 890,652, filed July 30, 1986 (now abandoned).

The present invention relates to a thermosettable imide compound. The invention relates also to an epoxy resin composition which comprises a thermosettable imide compound and epoxy resin and which is suitable for lamination and molding.

Hitherto, for sealing laminates and semiconductor elements such as IC, LSI, etc. used in apparatus for industry and people's livelihood, epoxy resins have been used.

With the laminates, however, there is a large change in dimension in the direction perpendicular to the substrate because of the low thermal resistance of the hardened product of the resins, so that there have been problems such as lowering in through-hole reliability, smear, etc.. With the sealing material for IC, LSI, etc. there was also a problem that when parts such as IC, LSI, etc. are connected to circuits by soldering, the laminates are cracked by the heat of solder because of the large thermal expansion of the material.

For improving the thermal resistance of such hardened products, a method to use aromatic imide compounds as a hardener may be thought of.

Generally, aromatic imide compounds are produced with aromatic tetracarboxylic acid anhydrides and aromatic diamines as materials. The well-known representative aromatic tetracarboxylic acid anhydrides include pyromellitic acid anhydride, benzophenonetetracarboxylic acid anhydride. The aromatic imide compounds obtained from these acid anhydrides, however, have the following problems. Generally, they are very low in solubility in low-boiling organic solvents, so that for dissolving them, it is necessary to use special high-boiling solvents such as dimethylformamide, dimethylacetamide, N-methylpyrrolidone, dimethyl sulfoxide, cresol, etc. and they are also poor in compatibility with epoxy resins, phenolic resins, amines, acid anhydrides, etc., so that it is difficult to attain improvements in performance by using epoxy resins, etc., together.

In view of the present situation, the inventors extensively studied about the imide compounds superior in solubility and compatibility, and as a result, found that the imide compounds having a structural unit represented by the general formula

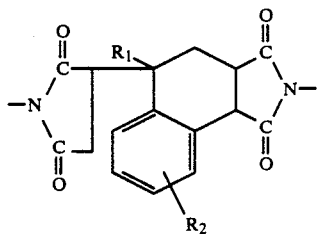

wherein $R_1$ represents a hydrogen atom or a $C_1$-$C_{10}$ alkyl group, and $R_2$ represents a hydrogen atom, a $C_1$-$C_{20}$ alkyl or alkoxyl group or a hydroxyl group, in the molecule satisfy the above objects, and also that the foregoing problems such as low thermal resistance, large changes in dimension, cracking of laminates by heat, etc. can be solved by using the imide compounds and epoxy resins together. The present inventors thus arrived at the present invention.

The present invention provides a thermosettable imide compound represented by the general formula (I),

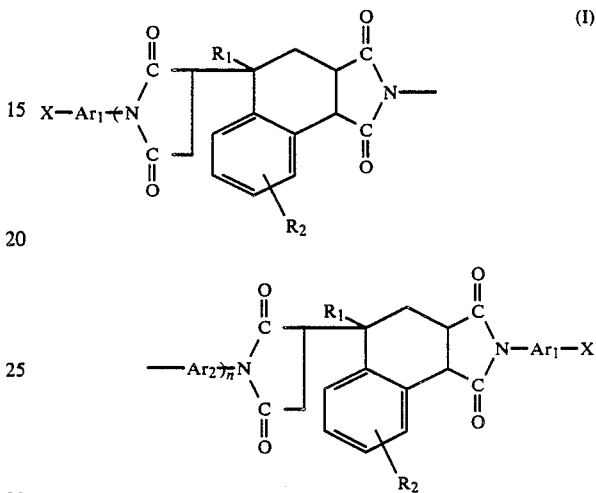

wherein X represents a hydroxyl or amino group, $Ar_1$ and $Ar_2$ independently represent an aromatic residue, $R_1$ represents a hydrogen atom or a $C_1$-$C_{10}$ alkyl group, $R_2$ represents a hydrogen atom, a $C_1$-$C_{20}$ alkyl or alkoxyl group or a hydroxyl group, and n represents a number of from 0 to 6, and also provides an epoxy resin composition containing the imide compound (B) and epoxy resins (A) as essential components.

Referring to $Ar_1$ and $Ar_2$ in more detail, they are independently a mononuclear or polynuclear divalent aromatic residue of which the aromatic ring may or may not be substituted with a lower alkyl group, a halogen atom, a lower alkoxyl group, etc.. Specifically, both $Ar_1$ and $Ar_2$ are the residue of an aromatic amine. More specifically, $Ar_1$ is the residue of an aromatic diamine.

Of the aromatic amines, the aromatic diamine includes for example,
4,4'-diaminodiphenylmethane,
3,3'-diaminodiphenylmethane,
4,4'-diaminodiphenyl ether,
3,4'-diaminodiphenyl ether,
4,4'-diaminodiphenylpropane,
4,4'-diaminodiphenyl sulfone,
3,3'-diaminodiphenyl sulfone,
2,4-tolylenediamine,
2,6-tolylenediamine,
m-phenylenediamine,
p-phenylenediamine,
benzidine,
4,4'-diaminodiphenyl sulfide,
3,3'-dichloro-4,4'-diaminodiphenyl sulfone,
3,3'-dichloro-4,4'-diaminodiphenylpropane,
3,3'-dimethyl-4,4'-diaminodiphenylmethane,
3,3'-dimethoxy-4,4'-diaminobiphenyl,
3,3'-dimethyl-4,4'-diaminobiphenyl,
1,3-bis(4-aminophenoxy)benzene,
1,3-bis(3-aminophenoxy)benzene, 1,4-bis(4-aminophenoxy)benzene,
2,2-bis(4-aminophenoxyphenyl)propane,
4,4'-bis(4-aminophenoxy)diphenyl sulfone,
4,4'-bis(3-aminophenoxy)diphenyl sulfone,
9,9'-bis(4-aminophenyl)anthracene,
9,9'-bis(4-aminophenyl)fluorene,
3,3'-dicarboxy-4,4'-diaminodiphenylmethane,
2,4-diaminoanisole, bis(3-aminophenyl)methylphosphine oxide,
3,3'-diaminobenzophenone,
o-toluidine sulfone,
4,4'-methylene-bis-o-chloroaniline,
tetrachlorodiaminodiphenylmethane,
m-xylylenediamine,
p-xylylenediamine,
4,4'-diaminostilbene,
5-amino-1-(4'-aminophenyl)-1,3,3-trimethylindane,
6-amino-1-(4'-aminophenyl)-1,3,3-trimethylindane,
5-amino-6-methyl-1-(3'-amino-4'-methylphenyl)-1,3,3-trimethylindane,
7-amino-6-methyl-1-(3'-amino-4'-methylphenyl)-1,3,3-trimethylindane,
6-amino-5-methyl-1-(4'-amino-3'-methylphenyl)-1,3,3-trimethylindane,
6-amino-7-methyl-1-(4'-amino-3'-methylphenyl)-1,3,3-trimethylindane, etc.

These compounds may be used alone or in combination.

On the other hand, the aromatic monoamine includes for example:
o-aminophenol, m-aminophenol, p-aminophenol,
6-amino-m-cresol, 4-amino-m-cresol,
2,2-(4-hydroxyphenyl-4-aminophenyl)propane,
2,2-(4-hydroxyphenyl-2'-methyl-4'-aminophenyl)propane,
2,2-(3-methyl-4-hydroxyphenyl-4'-aminophenyl)propane,
8-amino-1-naphthol, 8-amino-2-naphthol, 5-amino-1-naphthol,
4-amino-2-methyl-1-naphthol, etc.

These compounds may be used alone or in combination.

$R_1$ and $R_2$ are as defined above, but particularly preferably, $R_1$ is a $C_1$–$C_3$ alkyl group, and $R_2$ is a hydrogen atom or a $C_1$–$C_5$ alkyl group.

A method for producing the functional group-terminated imide compound of the present invention represented by the general formula (I) will be explained.

When a substituent X in the general formula (I) is an amino group, the imide compound (I) can be synthesized by reacting an excess of the foregoing aromatic diamine with a compound represented by the general formula (III):

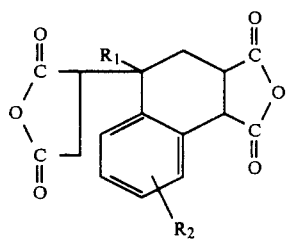

(III)

wherein $R_1$ and $R_2$ are as defined above, according to the common imidation technique.

When the substituent X in the general formula (I) is a hydroxyl group, the imide compound (I) can be synthesized by adding the foregoing aromatic monoamine having a hydroxyl group and the aromatic diamine to the compound (III) so that the molar ratio of aromatic diamine to compound (III) is n to (n+1) wherein n is as defined above, and besides the molar ratio of aromatic monoamine to compound (III) is 1 to (n+1), and carrying out the reaction according to the common imidation technique.

Referring to a method for producing the acid anhydride represented by the general formula (III), the compound (III) is obtained by reacting a compound represented by the general formula (IV):

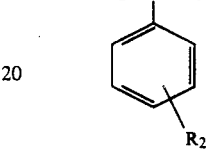

wherein $R_1$ and $R_2$ are as defined above, with maleic anhydride at a molar ratio of compound (IV) to maleic anhydride of 1 to 2 in the absence of a radical polymerization catalyst and in the presence or absence of a radical polymerization inhibitor. The compound represented by the general formula (IV) includes styrene, α-methylstyrene, α,p-dimethylstyrene, α,m-dimethylstyrene, isopropylstyrene, vinyltoluene, p-tert-butylstyrene, p-isopropenylphenol, m-isopropenylphenol, 1-methoxy-3-isopropenylbenzene, 1-methoxy-4-isopropenylbenzene, vinylxylene, etc.. These compounds may be used alone or in combination.

The functional group-terminated imide compounds of the present invention thus obtained are soluble in high concentrations in low-boiling solvents such as acetone, methyl ethyl ketone, methyl isobutyl ketone, methyl cellosolve, ethyl cellosolve, methylene chloride, chloroform, etc. Also, they are superior in compatibility with epoxy resins, phenolic resins, amines, acid anhydrides, etc.

The functional group-terminated imide compounds of the present invention are also thermosettable by mixing with epoxy resins, etc. The hardened product obtained is superior in thermal resistance, mechanical characteristics, solvent resistance, etc.

The epoxy resin used in the present invention is for example a compound having two or more epoxy groups in the molecule. Examples of the epoxy resin include the example glycidyl ether compounds derived from dihydric or more phenols [e.g., bisphenol A, bisphenol F, hydroquinone, resorcinol, phloroglucinol, tris(4-hydroxyphenyl)methane, 1,1,2,2-tetrakis(4-hydroxyphenyl)ethane] or halogenated bisphenols (e.g., tetrabromobisphenol A); novolak type epoxy resins derived from novolak resins which are reaction products of phenols (e.g., phenol, o-cresol) with formaldehyde; amine type epoxy resins derived from aniline,
p-aminophenol,
m-aminophenol,
4-amino-m-cresol,
6-amino-m-cresol,
4,4'-diaminodiphenylmethane,
3,3'-diaminodiphenylmethane,
4,4'-diamindiphenyl ether, 3,4'-diaminodiphenyl ether,
1,4-bis(4-aminophenoxy)benzene,
1,4-bis(3-aminophenoxy)benzene,
1,3-bis(4-aminophenoxy)benzene,
1,3-bis(3-aminophenoxy)benzene,
2,2-bis(4-aminophenoxyphenyl)propane,
p-phenylenediamine,
m-phenylenediamine,
2,4-tolylenediamine,
2,6-tolylenediamine,
p-xylylenediamine,
m-xylylenediamine,
1,4-cyclohexane-bis(methylamine),
1,3-cyclohexane-bis(methylamine),
5-amino-1-(4'-aminophenyl)-1,3,3-trimethylindane,
6-amino-1-(4'-aminophenyl)-1,3,3-trimethylindane,
etc.;

glycidyl ester compounds derived from aromatic carboxylic acids (e.g., p-oxybenzoic acid, m-oxybenzoic acid, terephthalic acid, isophthalic acid); hydantoin type epoxy resins derived from 5,5-dimethylhydantoin, etc.; alicyclic epoxy resins such as 2,2'-bis(3,4-epoxycyclohexyl)propane, 2,2-bis[4-(2,3-epoxypropyl)cyclohexyl]propane, vinylcyclohexene dioxide, 3,4-epoxycyclohexylmethyl-3,4-epoxycyclohexanecarboxylate, etc.; and other compounds such as triglycidyl isocyanurate, 2,4,6-triglycidoxy-S-triazine, etc. These epoxy resins may be used alone or in combination.

The epoxy resin composition of the present invention contains the epoxy resin explained above and the functional group-terminated imide compound of the present invention as essential components, and if necessary, it may further contain the well-known epoxy hardeners and hardening accelerators, fillers, flame retardants, reinforcing agents, surface-treating agents, pigments, etc.

The well-known epoxy hardeners include, for example, amine type hardeners such as the foregoing aromatic amines (e.g., xylylenediamine), aliphatic amines, etc.; polyphenols such as phenol novolak, cresol novolak, etc.; and acid anhydrides, dicyandiamide, hydrazides, etc. As to the proportion of the epoxy resin (A) to the functional group-terminated imide compound (B), such proportions are preferred that the total amount of (B) and other hardeners is 0.8 to 1.2 gram equivalents based on 1 gram equivalent of (A), and besides the amount of (B) is 0.4 to 1.2 gram equivalents based on 1 gram equivalent of (A). The hardening accelerators include for example amines [e.g., benzyldimethylamine, 2,4,6-tris(dimethylaminomethyl)phenol, 1,8-diazabicycloundecene], imidazole compounds (e.g., 2-ethyl-4-methylimidazole), boron trifluoride amine complexes, etc. The fillers include silica, calcium carbonate, etc.; the flame retardants include aluminum hydroxide, antimony trioxide, red phosphorus, etc.; and the reinforcing agents include fabrics comprising organic or inorganic fibers (e.g., glass fibers, polyester fibers, polyamide fibers, alumina fibers), non-woven fabrics, mats, papers and combinations thereof.

The present epoxy resin composition explained above gives hardened products having such an extremely high thermal resistance as can never be obtained by the prior art, and therefore, it is of industrially very high value as a material for lamination and molding.

The present invention will be illustrated in more detail with reference to the following examples, but it is not limited to these examples.

EXAMPLE 1

To a flask equipped with a stirrer, a thermometer and a cooling separator were added 29.7 g (0.15 mole) of 4,4'-diaminodiphenylmethane and 242 g of m-cresol, and after dissolving the diaminodiphenylmethane in the m-cresol, 48.5 g of xylene was added. After heating the resulting mixture to a temperature of 120° C., 31.4 g (0.1 mole) of 1-methyl-3,4-dicarboxy-1,2,3,4-tetrahydro-1-naphthalenesuccinic acid anhydride was added at this temperature, and after raising the temperature to 175° C., dehydration was continued at this temperature for 5 hours. After completion of the reaction, a hexane/isopropanol mixed solution was added to precipitate the reaction product.

The product was then washed two times with the same mixed solution and dried under reduced pressure to obtain an imide compound. This imide compound had a melting point of 241° C. and an amine equivalent of 634 g/eq.

EXAMPLE 2

A procedure was carried out in the same manner as in Example 1 except that 24.4 g (0.2 mole) of 2,4-tolylenediamine was used in place of 29.7 g (0.15 mole) of 4,4'-diaminodiphenylmethane, to obtain an imide compound. This compound had a melting point of about 220° C. and an amine equivalent of 353 g/eq.

EXAMPLE 3

A procedure was carried out in the same manner as in Example 1 except that 24.0 g (0.22 mole) of m-aminophenyl was used in place of 29.7 g (0.15 mole) of 4,4'-diaminodiphenylmethane, to obtain an imide compound. This compound had a melting point of about 210° C. and a hydroxyl equivalent of 249 g/eq.

The imide compounds obtained in Examples 1 to 3 are soluble in solvents such as acetone, MEK, methylene chloride, methyl cellosolve, etc.

EXAMPLE 4

A procedure was carried out in the same manner as in Example 1 except that 14.3 g (0.117 mole) of 2,4-tolylenediamine was used in place of 29.7 g (0.15 mole) of 4,4'-diaminodiphenylmethane, to obtain an imide compound. This compound had a melting point of over 300° C. and an amine equivalent of 1280 g/eq.

EXAMPLE 5

100 Grams of Sumi ® epoxy ELA-128 (bisphenol A type epoxy resin; epoxy equivalent, 187 g/eq; a product of Sumitomo Chemical Co.) and 163 g of the imide compound obtained in Example 1 were uniformly dissolved in 180 g of dimethylformamide. This solution was impregnated into glass cloth (WE 18K-BZ-2; a product of Nitto Boseki Co., Ltd.), which was then treated for 5 minutes in an oven kept at a temperature of 180° C. to obtain prepreg. Six pieces of prepreg and a copper foil (a product of Furukawa Circuit Foil Co.; TAI treatment, thickness, 35μ) were placed one upon another and press-molded at a temperature of 180° C. for 5 hours under a pressure of 50 kg/cm² to obtain a copper-lined laminate of 1 mm in thickness. The physical properties of this laminate were measured according to JIS C 6481 to obtain the result shown in Table 1.

EXAMPLE 6

A procedure was carried out in the same manner as in Example 5 except that 90 g of the imide compound obtained in Example 2 was used in place of the imide compound obtained in Example 1, and that the amount of dimethylformamide was changed from 180 g to 130 g, to obtain a laminate. The physical properties of this laminate are shown in Table 1.

EXAMPLE 7

A procedure was carried out in the same manner as in Example 5 except that 307 g of the imide compound obtained in Example 4 was used in place of the imide compound obtained in Example 1, and that the amount of dimethylformamide was changed from 180 g to 350 g to obtain a laminate. The physical properties of this laminate are shown in Table 1.

COMPARATIVE EXAMPLE 1

240 Grams of Sumi® epoxy ESA-011 (bisphenol A type epoxy resin; epoxy equivalent, 489 g/eq; a product of Sumitomo Chemical Co.), 9 g of dicyandiamide and 1 g of 2-phenyl-4-methyl-5-hydroxymethylimidazole were dissolved in a mixed solvent comprising 40 g of dimethylformamide, 60 g of ethylene glycol monomethyl ether and 60 g of methyl ethyl ketone. In the same manner as in Example 5, the resulting solution was impregnated into glass cloth, which was then treated for 5 minutes in an oven kept at a temperature of 160° C. to prepare prepreg. This prepreg was press-molded in the same condition as in Example 5 to prepare a laminate. The physical properties of the laminate are shown in Table 1.

physical properties of the hardened product obtained are shown in Table 2.

COMPARATIVE EXAMPLE 2

A procedure was carried out in the same manner as in Example 8 except that 56 g of the phenol novolak resin only was used as a hardener, and that the amount of silica, a filler, was changed from 427 g to 364 g, to obtain a hardened product. The physical properties of this hardened product are shown in Table 2.

TABLE 2

| Examples | | Example 8 | Comparative Example 2 |
|---|---|---|---|
| Tg | °C. | 240 | 170 |
| Thermal expansion coefficient (<Tg) | 1/°C. | $2.0 \times 10^{-5}$ | $2.6 \times 10^{-5}$ |
| Thermal expansion rate (20° to 260° C.) | % | 1.10 | 1.35 |
| Bending strength (20° C.) | kg/mm$^2$ | 14.7 | 14.8 |
| Bending strength (100° C.) | kg/mm$^2$ | 14.0 | 12.1 |
| Bending strength (150° C.) | kg/mm$^2$ | 12.4 | 9.0 |
| Bending strength (180° C.) | kg/mm$^2$ | 9.5 | 2.1 |

It is apparent from Tables 1 and 2 that the composition obtained according to the present invention has excellent thermal resistance, giving molded products having a high dimensional stability.

What is claimed is:

1. An epoxy resin composition containing an epoxy resin (A) and a functional group-terminated imide compound (B) represented by the general formula (II)

(II)

TABLE 1

| Example | | Example 5 | Example 6 | Example 7 | Comparative Example 1 |
|---|---|---|---|---|---|
| Tg | °C. | 220 | 235 | 241 | 124 |
| Expansion coefficient in the Z direction (Tg or less) | 1/°C. | $3.7 \times 10^{-5}$ | $3.6 \times 10^{-5}$ | $3.5 \times 10^{-5}$ | $5.7 \times 10^{-5}$ |
| Thermal expansion rate in the Z direction (20° to 220° C.) | % | 1.14 | 1.06 | 1.10 | 3.15 |
| Thermal expansion rate in the Z direction (20° to 260° C.) | % | 2.41 | 2.33 | 2.38 | >10 |
| Water absorption (after 24 hours' boiling) | % | 1.18 | 1.16 | 1.20 | 1.94 |
| Water abosrption (after 48 hours' boiling) | % | 1.29 | 1.24 | 1.29 | 2.18 |
| Resistance of copper foil to peeling | kg/m | 237 | 229 | 211 | 210 |
| Thermal resistance to soldering (300° C.) | Appearance | Pass | Pass | Pass | Swelling |

EXAMPLE 8

100 Grams of Sumi® epoxy ESCN-195XL (o-cresol novolak type epoxy resin, epoxy equivalent, 197 g/eq; a product of Sumitomo Chemical Co.), 62 g of the imide compound obtained in Example 2, 17 g of a phenol novolak resin, 1 g of 2,4,6-tris(dimethylaminomethyl)-phenol, 1 g of carnauba wax, 2 g of a silane coupling agent (SH-6040; a product of Toray Silicone Ltd.) and 427 g of silica were kneaded at a temperature of 100° C. for 5 minutes on a two-roll kneader, cooled and pulverized to produce a molding material. This molding material was press-molded at a temperature of 170° C. for 5 minutes under a pressure of 70 kg/cm$^2$ and hardened for 5 hours in an oven kept at a temperature of 180° C. The

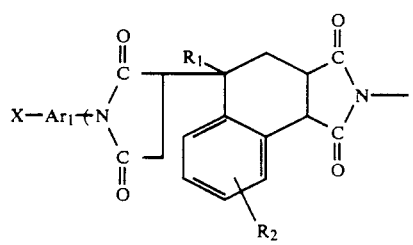

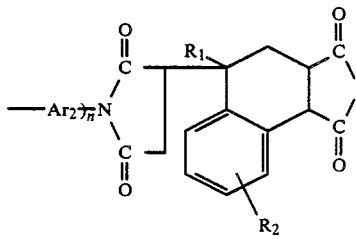

wherein X represents a hydroxyl or amino group, $Ar_1$ and $Ar_2$ independently represent an aromatic residue, $R_1$ represents a hydrogen atom or a $C_1$–$C_{10}$ alkyl group, $R_2$ represents a hydrogen atom, a $C_1$–$C_{20}$ alkyl or alkoxyl group or a hydroxyl group, and n represents a number of from 0 to 6, as essential components.

2. An epoxy resin composition as claimed in claim 1, wherein the imide compound (B) in which the terminal functional group X is an amino group is used.

3. An epoxy resin composition as claimed in claim 1 wherein $R_1$ is a $C_1$–$C_3$ alkyl group.

4. An epoxy resin composition as claimed in claim 1 wherein $R_2$ is a hydrogen atom or a $C_1$–$C_5$ alkyl group.

5. An epoxy resin composition as claimed in claim 2 wherein $R_1$ is a $C_1$–$C_3$ alkyl group.

6. An epoxy resin composition as claimed in claim 2 wherein $R_2$ is a hydrogen atom or a $C_1$–$C_5$ alkyl group.

* * * * *